United States Patent [19]
Van Hofwegen et al.

[11] Patent Number: 5,179,945
[45] Date of Patent: Jan. 19, 1993

[54] DEFIBRILLATION/CARDIOVERSION SYSTEM WITH MULTIPLE EVALUATION OF HEART CONDITION PRIOR TO SHOCK DELIVERY

[75] Inventors: Lloyd Van Hofwegen, New Brighton; Jean-Cheui Hsung, Shoreview; Daniel Huntwork, Vadnais Heights, all of Minn.

[73] Assignee: Cardiac Pacemakers, Inc., St. Paul, Minn.

[21] Appl. No.: 642,337

[22] Filed: Jan. 17, 1991

[51] Int. Cl.[5] .............................................. A61N 1/39
[52] U.S. Cl. .................................................. 128/419 D
[58] Field of Search ..................................... 128/419 D

[56] References Cited
U.S. PATENT DOCUMENTS

| | | | |
|---|---|---|---|
| 4,202,340 | 5/1980 | Langer et al. | 128/419 D |
| 4,210,149 | 7/1980 | Heilman et al. | 128/419 D |
| 4,375,817 | 3/1983 | Engle et al. | 128/419 D |
| 4,432,375 | 2/1984 | Angel et al. | 128/419 D |
| 4,576,170 | 3/1986 | Bradley et al. | 128/419 D |
| 4,614,192 | 9/1986 | Imran et al. | 128/419 D |
| 4,819,643 | 4/1989 | Menken | 128/419 P |
| 4,949,719 | 8/1990 | Pless et al. | 128/419 D |
| 4,971,058 | 11/1990 | Pless et al. | 128/419 D |

FOREIGN PATENT DOCUMENTS

8901802 3/1989 PCT Int'l Appl. ............. 128/419 D

*Primary Examiner*—William E. Kamm
*Attorney, Agent, or Firm*—Keck, Machin & Cate

[57] ABSTRACT

An automatic implantable defibrillator/cardioverter having a non-committed defibrillation/cardioversion algorithm. The defibrillator/cardioverter includes an ECG amplifier with automatic gain control (AGC) which detects the electrical activity of the heart for analysis by a cardiac condition detector. Logic is provided which receives input from the ECG amplifier and the cardiac condition detector for analyzing the heart activity. The non-committed defibrillation algorithm sensing begins upon the determination of an arrhythmia. The capacitor is charged while the heart activity is simultaneously monitored. After the capacitor is charged, a check is made on the duration of the last detected R-R interval while so charging the capacitor, and a comparison is made between this R-R interval and a preset value. If the last R-R interval is greater than the preset value, a non-committing period is entered which lasts approximately 2 seconds. The purpose of the non-committing period is to allow detection to monitor the arrhythmia further before making the decision to discharge the capacitor or dump the charge internally. If any R-R interval detected during this interval is less than PCLL, this indicates that the arrhythmia has not reverted and the capacitor charge is delivered to the patients, synchronously with the second R-wave of the fast R-R interval. If no rapid interval is detected during this time, a post intervention (PI) monitoring routine is entered at the end of the non-committing period to further monitor cardiac activity and shock if necessary.

27 Claims, 4 Drawing Sheets

DEFIBRILLATION/CARDIOVERSION SYSTEM WITH MULTIPLE EVALUATION OF HEART CONDITION PRIOR TO SHOCK DELIVERY

BACKGROUND OF THE INVENTION

The present invention relates to an implantable automatic defibrillator and more particularly to a feature in an implantable automatic defibrillator for diverting the charge on a defibrillator capacitor to an internal load.

In implantable cardiac treatment devices, such as an implantable defibrillator, a cardiac arrhythmia is detected based on sensed electrical and other activity of the heart. In defibrillation, the determination of a tachycardia, or fast beating heart, is indicative of impending ventricular fibrillation. Upon the determination of such an arrhythmia, a defibrillation capacitor is charged to a selected level for ultimately discharging and delivering an electrical shock to the heart.

Oftentimes, the arrhythmia of the heart is temporary and does not further develop into fibrillation, but reverts to normal sinus rhythm. This can occur while the defibrillation capacitor is charging or shortly after the capacitor has been charged. If the capacitor is discharged to a heart in normal sinus rhythm, the result could be detrimental, and at the worst put the heart into an arrhythmia. In addition, a high energy defibrillation shock normally causes some trauma to the patient; thus an unnecessary shock is to be avoided.

To avoid delivering an unnecessary defibrillation shock, it would be advantageous to delay the discharge of the defibrillation capacitor after it has been fully charged to allow further monitoring if there is an indication that the arrhythmia has reverted to normal sinus rhythm during the charging process.

Some defibrillation devices incorporate delays for manually disenabling the capacitor discharge. See for example U.S. Pat. Nos. to Bradley et al. (4,576,170) and Heilman et al. (4,210,149). These devices have built-in delays to allow the wearer to disenable the implantable device to prevent the delivery of a shock after the patient is audibly warned of an impending shock. The purpose of these devices is to allow the patient to override the implantable device in the event that a false detection occurs.

These devices fail in that a truly accurate examination of the heart activity is not made when disenabling the device. Therefore, it is possible to ignore a malignant heart condition.

SUMMARY OF THE INVENTION

It is a primary object of the present invention to provide a non-committed defibrillation/cardioversion system and algorithm in an implantable defibrillator whereby the heart activity is monitored during and after the charging of a defibrillation capacitor to further evaluate the heart condition before discharging the defibrillation capacitor.

The present invention relates to an automatic implantable defibrillator having a non-committed defibrillation system algorithm. The system and algorithm are non-committed in that, after the defibrillation capacitor has been charged, the heart condition is further evaluated and a shock is not delivered to the patient if it is no longer necessary. The defibrillator includes an ECG amplifier with automatic gain control (AGC) which detects the electrical activity of the heart for analysis by a cardiac condition detector. Logic is provided which receives input from the ECG amplifier and the cardiac condition detector for analyzing the heart activity.

The cardiac condition detector is connected to a charging circuit for charging at least one defibrillation capacitor. (One capacitor will be referred to hereinafter, but it is to be understood that a plurality of capacitors may be provided.) A triggering circuit is provided which is controlled by the logic to actuate the discharge of the defibrillation capacitor to the heart. In addition, a manual disenable circuit is provided which can override the logic to prevent discharge of the defibrillation capacitor.

The non-committed defibrillation algorithm (hereinafter also referred to as the abort algorithm) operates with R-wave sensing during the charging of the defibrillation capacitor and is accomplished by firmware embodied by the logic. The algorithm begins upon the determination of an arrhythmia. The capacitor is charged while the heart activity is simultaneously monitored. Once the capacitor has been charged to the selected level, the first of two possible delays occurs.

The first delay is programmable but is expected to be approximately 200 msec long. During this time the ECG amplifier is allowed to settle after the charging circuit is deactivated to terminate any effects that the AGC has in the ECG amplifier. Further, this settling time is required because capacitor discharge is desired to be synchronized with the sensing of an R-wave; the ECG amplifier can better detect R-waves after the charging circuit has settled. Another reason for the first delay is to allow manual diversion of the capacitor charge to an internal load should it otherwise be decided to divert the charge of the capacitor. At the end of the first delay, a check is made on the duration of the last R-R interval detected while charging the capacitor. A comparison is made between this R-R interval and a programmable tachycardia primary rate cycle length limit (PCLL).

If the last R-R interval is greater than PCLL, a second delay is initiated. This second delay is programmable, is referred to as the non-committing period, and is expected to be set at approximately 2 seconds. The purpose of the second delay is to allow detection to monitor the cardiac activity further after capacitor discharge but before making the decision to discharge the capacitor or dump the charge internally. If any R-R interval detected during this interval is less than PCLL, this indicates that the arrhythmia has not reverted and that the capacitor charge is to be delivered to the patient immediately, but synchronously. If no rapid interval is detected during this time, the shock is not delivered and a post intervention (PI) monitoring routine is entered at the end of the non-committing period. The PI routine is entered also after the synchronous shock.

During the PI routine, further cardiac condition detection is performed and if the arrhythmia has reverted, then the capacitor charge is dumped internally. If, however, the arrhythmia has not reverted, the capacitor is brought up to an appropriate level (should leakage have occurred), a synchronization window is initiated, and the capacitor is discharged synchronized to an R-wave if one is detected during the synchronization window, and otherwise the capacitor is discharged at the end of the synchronization window.

If the last R-R interval is less than or equal to PCLL, a check is made on the time interval from the most recently sensed R-wave (PTOC) during capacitor charging to the end of the 200 msec interval. One of two results are possible. First, if this time interval is greater than PCLL, the non-committing period is entered and the procedure described therewith is followed. Second, if this time interval is less than or equal to PCLL, the synchronization window is entered to shock the heart synchronously if possible.

The abort algorithm of the present invention can be used in cardioverting a high rate tachycardia (often known as a malignant tachyarrhythmia) with a relatively low energy and synchronized shock, as well as ventricular fibrillation with a relatively high energy synchronous or asynchronous shock.

The above and other objects and advantages of the present invention will become more apparent when reference is made to the following description taken in conjunction with the accompanying drawings.

DETAILED DESCRIPTION OF THE DRAWINGS

Figure 1:
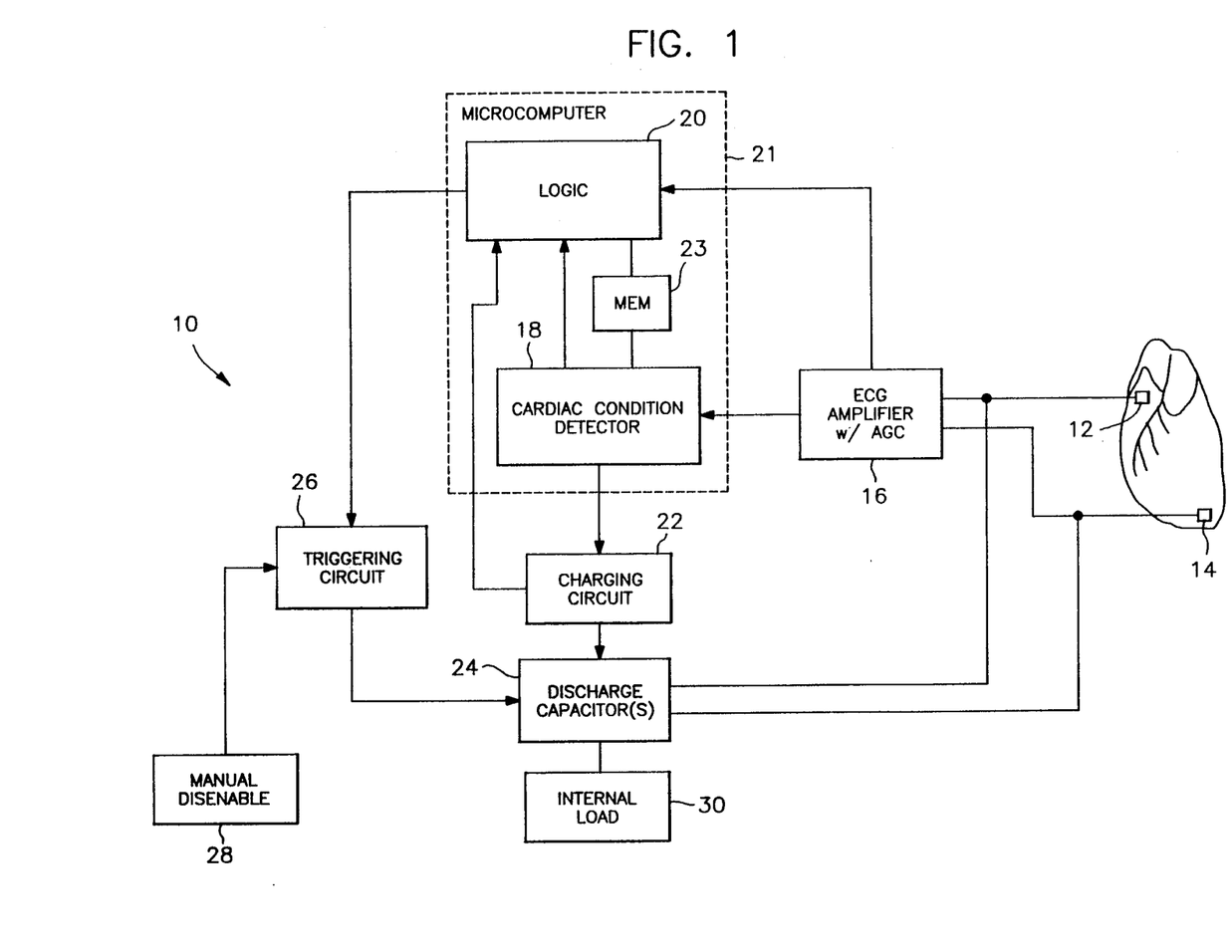
FIG. 1 is a schematic block diagram illustrating the various components of the non-committed defibrillation system of the present invention.

Referring first to FIG. 1, the various components of the present invention will be described. The non-committed defibrillation system, generally showed at 10, includes sensing/discharging electrodes 12 and 14 mounted on or about the heart which are connected to ECG sense amplifier 16. The ECG amplifier 16 may contain one or more sense channels, but also includes automatic gain control (AGC).

The ECG amplifier 16 is connected to a cardiac condition detector 18 and to logic 20 for analyzing the heart activity detected by the ECG amplifier 16. Logic 20 can be embodied as software, firmware, or in the form of conventional logic gates and circuits. A detailed description of a flow diagram of logic 20 is set forth hereinafter. The cardiac condition detector 18 includes the ability to measure time intervals between successive R-waves as well as other functions well known in the art for diagnosing the function of the heart.

The logic 20 and cardiac condition detector 18 may be incorporated as one unit, such as for example, in a microcomputer 21 as shown, but regardless, include means for performing rate detection such as determining the R-R interval, probability density function (PDF) detection, and other arrhythmia monitoring schemes which are known in the art, and which are not part of the essence of the present invention. In addition, a memory 23 is also provided in the microcomputer 21, as is well known in the art, for storing cardiac condition information such as R-R wave intervals and programmable data.

A charging circuit 22 is provided for charging the discharge capacitor 24. The charging circuit is connected to logic 20 for communicating therewith. Also connected to logic 20 is a triggering circuit 26 for controlling the discharge of the capacitor 24. In addition, a manual disenable 28 is provided for causing the triggering circuit 26 to prevent the capacitor 24 from discharging to the electrodes 12 and 14. The triggering circuit 26 triggers the capacitor 24 to discharge through the electrodes 12 and 14 or through an internal load 30.

Figure 2:
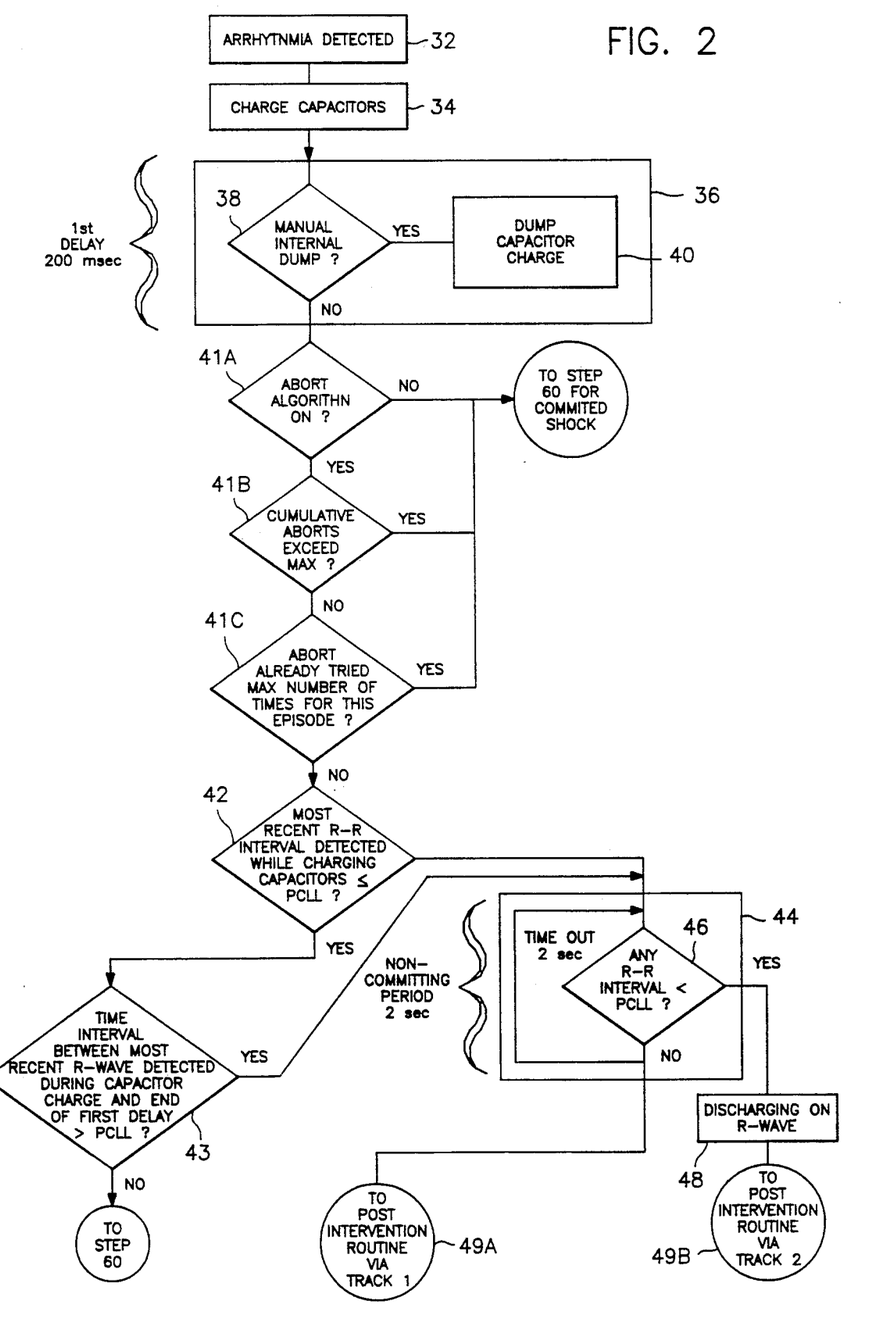
FIGS. 2 and 3 are flow charts illustrating the procedural steps for implementing the abort algorithm of the present invention.
Figure 3:
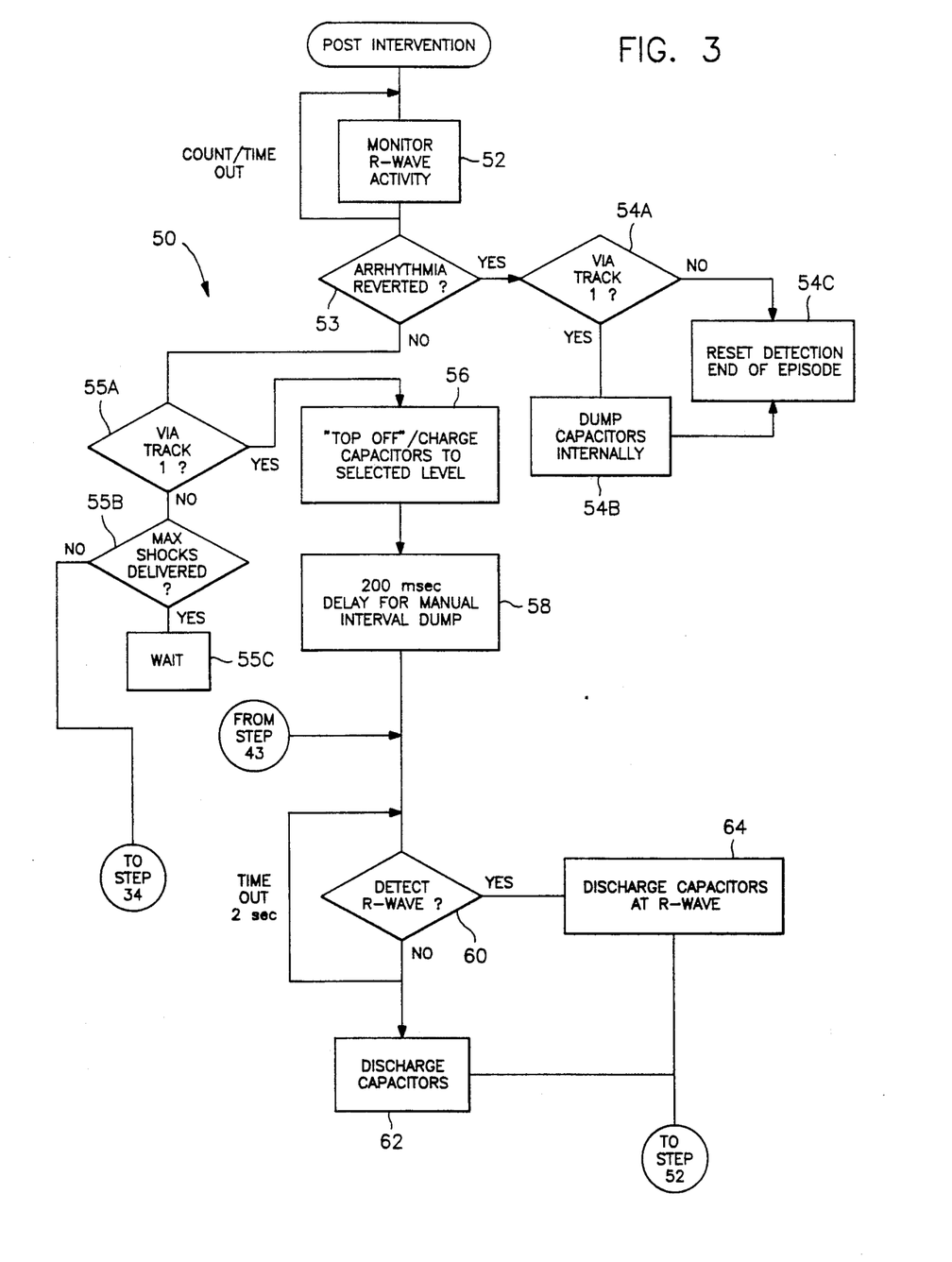
Figure 4:
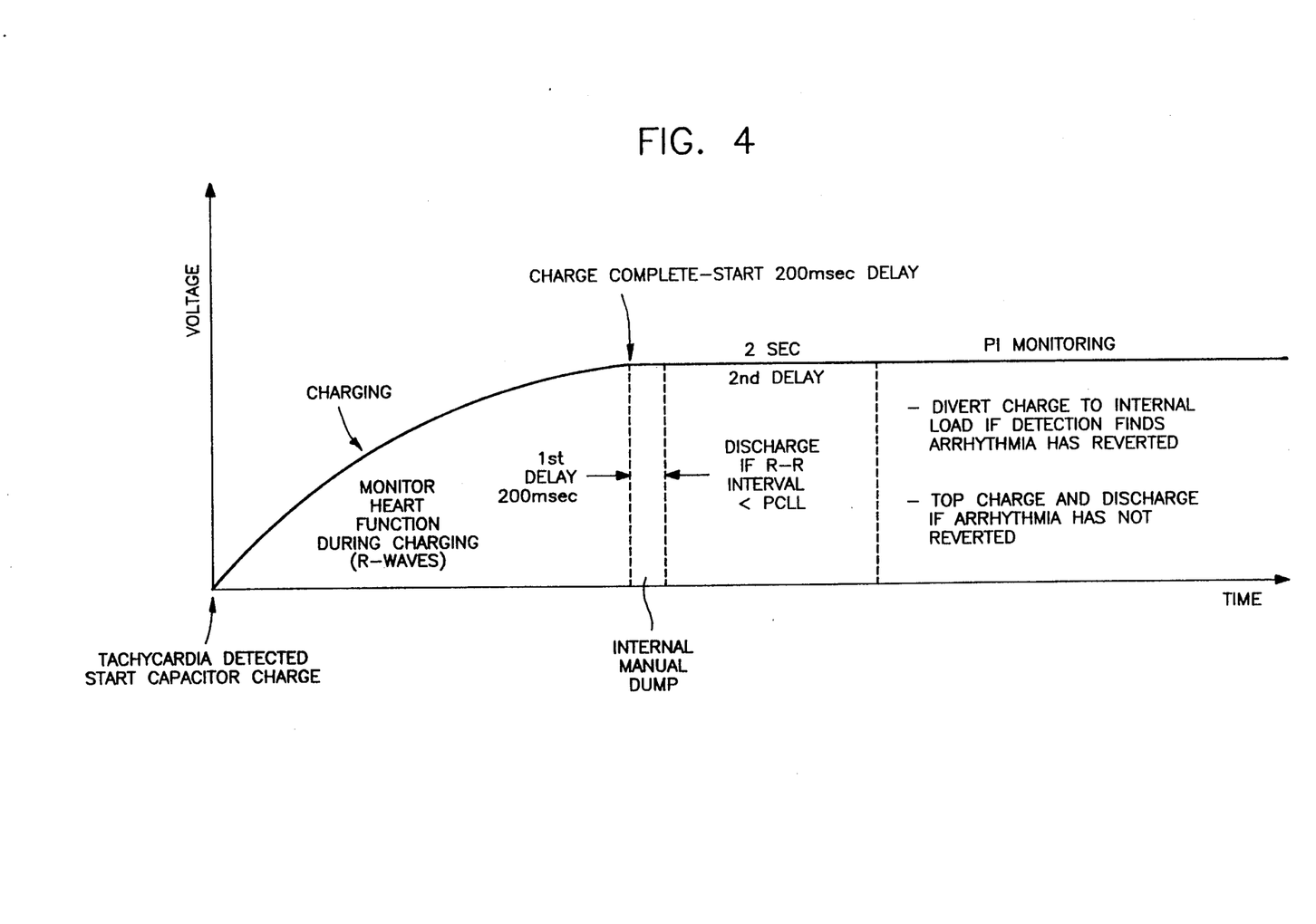
FIG. 4 is an illustration of the particular time intervals of the abort algorithm related to the charging and discharging of a defibrillation capacitor.

Referring now to FIGS. 2-4, together with FIG. 1, the abort algorithm will now be described. FIGS. 2 and 3 illustrate the logic flow pattern embodied by logic 20 of the system illustrated in FIG. 1. The ECG sense amplifier 16 senses the electrical activity of the heart via electrodes 12 and 14. This information is analyzed by the cardiac condition detector 18. The abort algorithm is entered once an initial determination is made that the heart is in an arrhythmia. If it is determined that a tachycardia or other arrhythmia is present at step 32 by some other means or mechanism not considered part of the present invention, the capacitor 24 is charged to a selected level at step 34 to ultimately defibrillate the heart. Also, while the capacitor 24 is being charged in step 34, the electrical activity of the heart is continuously sensed by the ECG amplifier 16 to monitor the R-waves. Once the capacitor 24 is fully charged, a first delay of 200 msec is initiated at step 36.

The first delay is programmable but preferably lasts approximately 200 msec. During this time, the ECG sense amplifier 16 is allowed to settle to facilitate discharge of the capacitor to be synchronized with a R-wave if necessary. Also, this time window permits block out any effect that the charging circuit 22 may have on the automatic gain control circuitry in the ECG sense amplifier 16. In addition, a manual dump at step 38 can be accomplished by the manual disenable 28 during this time window should it be determined by a physician, for example, that it is not desirable to deliver the shock. If this latter step is chosen, the dump is made at step 40 to the internal load 30.

Otherwise, the preliminary steps 41A–41C are entered. Step 41A illustrates the selective nature of the abort algorithm. The physician/technician can program the device to employ or not to employ the abort algorithm. When not activated, only committed shocks would be delivered. In step 41B, it is determined whether a maximum number of aborts has already been effected during the current state of operation of the algorithm. In addition, as shown in step 41C, there is preferably a maximum number of times that the algorithm can enter the non-committing period (referred to hereinafter). While this parameter can be reset by a physician/ technician, it is normally fixed for the period of time between physician check-ups. In effect, the algorithm will permit only so many delays (and capacitor diversions) before going fully committed. Therefore, patients with spaced short-run ventricular tachyarrhythmias will not cause the device to waste battery charge due to repeated charge and subsequent internal discharge of the capacitor. As indicated in FIG. 2, once this maximum value is met, the device will deliver committed shocks. The microcomputer 21 keeps track of the various parameters specified in steps 41A–41C.

If the abort algorithm is turned on and none of the maximums specified in steps 41B and 41C are met, the decision step 42 is entered for making a comparison of the most recent R-R interval, detected while charging the capacitors in step 34 (stored in memory 23), with a tachycardia primary rate cycle length limit (PCLL). One of two branches is taken depending on the result at step 42.

If this R-R interval is greater than PCLL, a second delay is initiated at step 44. This second delay is programmable and can last up to, but no more than 2 seconds. The purpose of this delay is to allow further monitoring of the heart activity before a decision to discharge or dump the capacitor 24 is made. This delay period is termed a non-committing period during which discharge of the capacitor 24 is not triggered unless a certain cardiac condition is detected. At this point, the indication after the first delay is that the arrhythmia might revert spontaneously. R-wave activity is constantly monitored by the cardiac condition detector 18 during the non-committing period.

During the non-committing period, if any R-R interval detected is less than PCLL, at step 46, discharge of the defibrillation capacitor 24 is immediately effected in step 48 on the second R-wave of the first fast interval detected. If, on the other hand, the result in step 46 is negative, the post intervention (PI) routine 50 shown in FIG. 3 is entered at the end of the non-committing period via a first track indicated in step 49A. The charge on the capacitor 24 is allowed to remain at this time. Also, after the shock delivered in step 48, the PI routine is entered via a second track indicated in step 49B.

Referring now to FIG. 3, in the PI routine, the electrical activity of the heart is continuously monitored at step 52 for a certain present period of time or certain present number of cardiac cycles. After the time-out or count-out in step 52, based on the continuously monitored cardiac activity, a determination is made at step 53 to determine if the arrhythmia has reverted. The details of steps 52 and 53 may involve many types of cardiac analysis not considered a part of the present invention. If the arrhythmia has reverted, it is determined in step 54A whether the PI routine was entered via track 1 (step 49A) or track 2 (step 49B). If the answer to the inquiry in step 54A is affirmative, then the triggering circuit 26 triggers the discharge of capacitor 24 through the internal load 30 at step 54B.

If it is detected in step 53 that the arrhythmia has not reverted, then it is determined in step 55A whether the PI routine was entered via track 1 (step 49A) or track 2 (step 49B). An affirmative response in step 55A will cause the algorithm to continue from step 56. A negative response in step 55A will follow to step 55B in which it is determined if a programmable maximum number of shocks has been exceeded for a single arrhythmia episode. If this maximum is met, the algorithm enters a "wait" state as shown at step 55C during which time the algorithm can be reset by a physician/technician or by spontaneous reversion to normal heart rhythm. During the "wait" state, if the heart rate remains below the value of PCLL, the algorithm is reset. Thereafter, any new arrhythmia is considered a new arrhythmic episode whereas if the current arrhythmic state does not revert, the "wait state is continued but the heart rate is monitored and if the rate decreases to below PCLL, the algorithm resets. Otherwise, the capacitor is again charged in step 34.

Should it be found in step 55A that the PI routine was entered via track 1, the charging circuit 22 is activated to ensure that the capacitor 24 is fully charged to the selected or appropriate level by effectively "topping off" the charge on the capacitor 24 at step 56. This step is sometimes necessary if the capacitor charge has leaked subsequent its initial charging or a higher energy shock is necessary if the arrhythmia has accelerated as determined in step 52. Thereafter, an optional 200 msec delay is entered at step 58 to allow for internal manual dump much like that shown at steps 38 and 40 in FIG. 2. If no internal dump is made, a synchronization window is entered at steps 60, 62 and 64. In the synchronization window, a shock is delivered synchronized to an R-wave if one is detected. The term synchronized is intended to mean simultaneous with an R-wave or a programmed period of time after an R-wave.

If after the first delay in step 42, it is determined that the most recent R-R interval detected while charging the capacitor 24 in step 34 is less than or equal to PCLL, the branch on the left side of FIG. 2 is taken to step 43. In step 43, a check is made on the time interval from the most recent R-wave (PTOC) detected while charging the capacitor 24 in step 34 to the end of the 200 msec first delay interval. The purpose of this comparison is that any occurrence of an R-wave during the first delay, whether or not detected, is considered to be fast provided the interval is less than PCLL even if it occurs at the end of the first delay. Consequently, if this interval is less than or equal to the PCLL, there is no indication that the heart rhythm is still not abnormally fast, and the algorithm goes to step 60 in FIG. 3, and shocks the heart synchronously if possible and otherwise asynchronously. Otherwise, the non-committing period at step 44 is entered and the steps there are executed as previously described.

The abort algorithm of the present invention allows a precise determination of whether a detected arrhythmia has subsequently reverted before delivering a discharge to the patient. Therefore, unnecessary electrical shocks are avoided, preventing trauma. Several modifications of the algorithm as described above can be made. First, parameters such as PCLL, the first delay, the duration of the non-committing period and the duration of the synchronization window may be programmable or may vary dynamically with changes in cardiac activity. In this regard, the terms preset or predetermined are meant to include variable such as dynamically changing. Furthermore, conditions such as the comparison in step 46, may be modified so as to require several (a predetermined or variable number) of fast R-R intervals. Accordingly, other tests or analysis of the cardiac activity can be made during the non-committing period to trigger or inhibit discharge of the defibrillation capacitors to the heart. In this regard, physiological indicators of cardiac arrhythmias such as, blood pressure or oxygenation, can be employed in the algorithm in addition to or in substitution for heart rate. It is also possible to operate the algorithm without the first delay period of step 36. In this case, the algorithm would be implemented without step 43 so that a positive response in step 43 would follow directly to step 60.

The above description is intended by way of example only and is not intended to limit the present invention in any way except as set forth in the following claims.

What is claimed is:

1. A method for defibrillating/cardioverting the heart comprising the steps of:
   (a) sensing the electrical activity of the heart including the interval between successive R-waves of the ECG;
   (b) comparing the interval between successive R-waves with a preset value corresponding to an interval indicative of a heart arrhythmia, to detect heart arrhythmias;
   (c) charging a defibrillation capacitor to a predetermined voltage level upon detecting an arrhythmia of the heart;

(d) storing the interval between successive R-waves during the step of charging the defibrillation capacitor;

(e) providing a first delay of a first predetermined period of time subsequent to said capacitor being charged to said predetermined level;

(f) comparing the stored interval between successive R-waves detected during the charging step with said preset value after said first delay;

(g) providing a second delay of a second predetermined period of time if said stored interval between successive R-waves is greater than said preset value as determined in step (f);

(h) comparing intervals between successive R-waves detected during the second delay with said preset value; and (i) discharging said defibrillation capacitor through the heart if any interval between successive R-waves detected during the second delay is less than said preset value as determined in step (h).

2. The method of claim 1, wherein said step (i) of discharging further comprises the step of synchronizing discharge with the second of the R-waves that define the first R-R interval less than said preset value, if such an interval occurs.

3. The method of claim 1, and further comprising the steps of:

(j) determining a time interval between the last R-wave detected during the step of charging and the end of said first delay if said stored interval is not greater than said preset value as determined in step (f);

(k) comparing said time interval of step (j) with a preset time interval; and (l) performing steps (g) - (i) if said time interval of step (j) exceeds said preset time interval as determined in step (k).

4. The method of claim 3, and further comprising the steps of:

(m) determining whether the detected arrhythmia has reverted if no interval between successive R-waves is less than said preset value as determined in step (h) or after the step (i) of discharging;

(n) diverting said predetermined voltage level of said defibrillation capacitor to an internal load if the arrhythmia has reverted as determined in step (m);

(o) providing a synchronization time window of a third predetermined period of time if a detected arrhythmia has not reverted as determined in step (m);

(p) detecting an R-wave during said synchronization time window;

(q) discharging said defibrillation capacitor at the occurrence of a detected R-wave in step (p); and (r) discharging said defibrillation capacitor at the end of said synchronization time window if no R-wave is detected during the synchronization time window.

5. The method of claim 4, and further comprising the step of ensuring that the charge on said defibrillation capacitor is at an appropriate voltage level if a detected arrhythmia has not reverted as determined in step (m).

6. The method of claim 4, wherein said third predetermined period of time is 2 seconds.

7. The method of claim 1, and further comprising the step of diverting said predetermined voltage level of said capacitor to an internal load during said first delay should an operator desire to prevent discharge to the heart of a patient.

8. The method of claim 1, wherein said first predetermined period of time is 200 milliseconds and said second predetermined period of time is 2 seconds.

9. The method of claim 1, wherein said step of storing includes storing successive R-R intervals and retaining only the last interval detected.

10. A system for defibrillating/cardioverting the heart comprising:

means for sensing the electrical activity of the heart including the interval between successive R-waves of the ECG;

means for detecting an arrhythmia of the heart;

means for storing the interval between successive R-waves;

defibrillation capacitor means;

means for charging said defibrillation capacitor means to a predetermined voltage level upon detecting an arrhythmia of the heart using said means for detecting;

means for triggering the discharge of said defibrillation capacitor means; and logic means including means for providing a first delay of a first predetermined period of time subsequent to said capacitor being charged to said predetermined level means for providing a second delay of a second predetermined period of time subsequent to said first delay; means for comparing the stored interval between successive R-waves detected during charging of the defibrillation capacitor means with a preset value during said first delay; means for entering said second delay of said second predetermined period of time if said stored interval between successive R-waves is greater than said preset value; and means for discharging said defibrillation capacitor to the heart if any interval between successive R-waves is less than said preset value during said second delay.

11. The system of claim 10, wherein said logic means further comprises means for determining a variable time interval between the last R-wave detected while charging the defibrillation capacitor means and the end of said first delay of said first predetermined period of time if said stored interval of successive R-waves is not greater than said preset value during said first delay, and compares said variable time interval with a preset time interval to enter said second delay if said variable time interval exceeds said preset time interval.

12. The system of claim 11, and further comprising an internal load, and wherein said logic means further comprises means for determining if a detected arrhythmia has reverted if no R-R interval detected during the second delay is less than said preset value or after discharge of the defibrillation capacitor means if an R-R interval is less than said preset value, and operates the means for triggering to divert said predetermined voltage level of said defibrillation capacitor to said internal load if the arrhythmia has reverted, the logic means further providing a synchronization time window of a third predetermined period of time if a detected arrhythmia has not reverted, said means for sensing detecting an R-wave during said third predetermined period of time and said logic means operating the means for triggering to effect discharge of said defibrillation capacitor at the occurrence of a detected R-wave during said synchronization time window or effecting discharge of said defibrillation capacitor at the end of said synchronization time window if no R-wave is detected during said third predetermined period of time.

13. The system of claim 12, wherein said logic means further comprises means for triggering said means for charging to charge said defibrillation capacitor means to an appropriate voltage level if a detected arrhythmia has not reverted after said second delay and charge on the defibrillation capacitor means has leaked to below the predetermined voltage level.

14. The system of claim 12, and further comprising memory means for programming said logic means wherein said first predetermined period of time is 200 milliseconds and said second predetermined period of time is 2 seconds.

15. The system of claim 12, wherein said third predetermined period of time is two seconds.

16. A method of non-committed defibrillation/cardioversion of the heart comprising the steps of:
(a) sensing the electrical activity of the heart including the interval between successive R-waves of the ECG;
(b) comparing the interval between successive R-waves with a first preset value and a second preset value, each of said first and second preset values corresponding to an interval indicative of a heart arrhythmia, to detect heart arrhythmias;
(c) charging a defibrillation capacitor to a predetermined voltage level upon detecting an arrhythmia of the heart;
(d) storing the interval between successive R-waves during the step of charging the defibrillation capacitor;
(e) comparing the stored interval between successive R-waves detected during the charging step with said first preset value;
(f) providing a non-committing period of a first predetermined period of time if said stored interval between successive R-waves is greater than said first preset value as determined in step (e);
(g) comparing intervals between successive R-waves detected during the non-committing period with the second preset value; and
(h) discharging said defibrillation capacitor through the heart if any interval between successive R-waves detected during the non-committing period is less than said second preset value as determined in step (g).

17. The method of claim 16, wherein the first preset value and the second preset value are equal.

18. The method of claim 17, wherein the first preset value and the second preset value are equal to a tachycardia primary rate cycle length limit which corresponds to a threshold cardiac rate at which the heart is deemed to be in tachycardia.

19. The method of claim 16, wherein said step (h) of discharging further comprises the step of synchronizing discharge with the second of the R-waves that define a first interval of successive R-waves less than said second preset value, if such an interval occurs.

20. The method of claim 16, and further comprising the steps of:
(i) providing a synchronization time window of a second predetermined period of time if said stored interval of successive R-waves is not greater than said first preset value as determined in step (e);
(j) detecting an R-wave during said synchronization time window; and
(k) discharging said defibrillation capacitor synchronized to a detected R-wave in step (j) and otherwise discharging the defibrillation capacitor at the end of the synchronization time window if no R-wave is detected.

21. The method of claim 16, and further comprising the steps of:
(l) determining whether the detected arrhythmia has reverted if no interval between successive R-waves is less than said second preset value as determined in step (g) and after the step (h) of discharging;
(m) diverting said predetermined voltage level of said defibrillation capacitor to an internal load if the arrhythmia has reverted as determined in step (l);
(n) providing a synchronization time window of a second predetermined period of time if a detected arrhythmia has not reverted as determined in step (l);
(o) detecting an R-wave during said synchronization time window;
(p) discharging said defibrillation capacitor at the occurrence of a detected R-wave in step (o); and
(q) discharging said defibrillation capacitor at the end of said synchronization time window if no R-wave is detected during the synchronization time window.

22. The method of claim 16, wherein said step of storing includes storing successive R-R intervals and retaining only the last interval detected.

23. A method for defibrillating/cardioverting the heart, according to the existence of first and second predetermined conditions of the heart, said method comprising the steps of:
(a) sensing a physiological indicator of an arrhythmia;
(b) detecting an arrhythmia of the heart based on the physiological indicator;
(c) charging a defibrillation capacitor to a predetermined voltage level upon detecting an arrhythmia of the heart;
(d) storing data related to the cardiac function of the heart during the step of charging;
(e) detecting whether the first predetermined condition of the heart occurs during the step of charging;
(f) providing a non-committing period of a first predetermined period of time if the first predetermined condition of the heart does not occur during the step of charging as determined in step (e);
(g) detecting whether the second predetermined condition of the heart occurs during said non-committing period based on the physiological indicator; and
(h) discharging said defibrillation capacitor through the heart if said second predetermined condition of the heart is detected during said non-committing period as determined in step (g).

24. The method of claim 23, and wherein said first predetermined condition comprises a time interval of consecutive R-waves being less than a preset value corresponding to a time interval indicative of a heart arrhythmia.

25. The method of claim 23, wherein said second predetermined condition comprises a time interval of consecutive R-waves occurring during the non-committing period being less than a preset value corresponding to a time interval indicative of a heart arrhythmia.

26. The method of claim 23, and further comprising the steps of:

(i) providing a synchronization time window of a second predetermined period of time if said first predetermined condition is detected as determined in step (e);

(j) detecting an R-wave during said synchronization time window; and (k) discharging said defibrillation capacitor synchronized to a detected R-wave in step (j) and otherwise discharging the defibrillation capacitor at the end of the synchronization time window if no R-wave is detected.

27. The method of claim 23, and further comprising the steps of:

(l) determining whether the detected arrhythmia has reverted if the second predetermined condition is not detected as determined in step (g) and after the step (h) of discharging;

(m) diverting said predetermined voltage level of said defibrillation capacitor to an internal load if the arrhythmia has reverted as determined in step (l);

(n) providing a synchronization time window of a second predetermined period of time if a detected arrhythmia has not reverted as determined in step (l);

(o) detecting an R-wave during said synchronization time window;

(p) discharging said defibrillation capacitor at the occurrence of a detected R-wave in step (o); and (q) discharging said defibrillation capacitor at the end of said synchronization time window if no R-wave is detected during the synchronization time window.

* * * * *